United States Patent
Ehr et al.

(10) Patent No.: US 6,652,471 B2
(45) Date of Patent: Nov. 25, 2003

(54) PRESSURE-SENSING GUIDEWIRE HAVING IMPROVED TORQUE

(75) Inventors: Timothy G. J. Ehr, Elk River, MN (US); Bruce Howard Asmus, Minnetonka, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 26 days.

(21) Appl. No.: 09/995,928

(22) Filed: Nov. 28, 2001

(65) Prior Publication Data

US 2003/0100838 A1 May 29, 2003

(51) Int. Cl.[7] ............. A61B 5/00; A61B 6/00; A61B 5/02; A61M 25/00; A61M 5/00
(52) U.S. Cl. ............. 600/585; 600/433; 600/434; 600/485; 604/264; 604/523; 604/524; 604/525; 604/533
(58) Field of Search .............. 600/585, 481, 600/485, 486, 433, 434, 435; 604/93.01, 264, 523, 524, 533, 525

(56) References Cited

U.S. PATENT DOCUMENTS

| | | | |
|---|---|---|---|
| 4,924,877 A | 5/1990 | Brooks | |
| 4,953,553 A | 9/1990 | Tremulis | |
| 4,957,117 A | 9/1990 | Wysham | .............. 604/95 |
| 5,050,606 A | 9/1991 | Tremulis | .............. 128/637 |
| 5,423,331 A | 6/1995 | Wysham | .............. 128/772 |
| 5,450,853 A | 9/1995 | Hastings et al. | |
| 5,558,643 A | 9/1996 | Samson et al. | .............. 604/96 |
| 5,706,826 A | 1/1998 | Schwager | |
| 5,836,885 A | 11/1998 | Schwager | .............. 600/486 |
| 5,851,189 A | 12/1998 | Forber | .............. 600/585 |
| 5,873,835 A | 2/1999 | Hastings et al. | .............. 600/488 |
| 5,916,177 A | 6/1999 | Schwager | |
| 5,964,714 A | 10/1999 | Lafontaine | |
| 6,066,114 A | 5/2000 | Goodin et al. | .............. 604/102 |
| 6,074,378 A * | 6/2000 | Mouri et al. | .............. 604/523 |
| 6,106,488 A | 8/2000 | Fleming et al. | .............. 600/585 |
| 6,183,424 B1 | 2/2001 | Schwager | |
| 6,190,332 B1 | 2/2001 | Muni et al. | .............. 600/585 |
| 6,206,834 B1 * | 3/2001 | Schwager | .............. 600/485 |

FOREIGN PATENT DOCUMENTS

| EP | 0397173 A1 | 11/1990 |
|---|---|---|
| EP | 0879617 A1 | 11/1998 |

OTHER PUBLICATIONS

International Search Report dated Mar. 18, 2003.

* cited by examiner

Primary Examiner—Max F. Hindenburg
Assistant Examiner—Navin Natnithithadha
(74) Attorney, Agent, or Firm—Marshall, Gerstein & Borun LLP

(57) ABSTRACT

A pressure-sensing guidewire assembly with improved stiffness and torquability is disclosed. The guidewire assembly includes an elongated tubular member having a lumen extending therethrough. The lumen receives a torque enhancing mandrel that adds stiffness and torquability to the elongated tubular member. The torque enhancing member and elongated tubular member may have an atraumatic spring tip.

15 Claims, 3 Drawing Sheets

PRESSURE-SENSING GUIDEWIRE HAVING IMPROVED TORQUE

FIELD OF THE INVENTION

The present invention generally relates to intravascular medical devices and methods for sensing and monitoring fluid pressure. More specifically, the present invention relates to intravascular diagnostic devices that consist of hollow tubes or wires used to sense and monitor intravascular fluid pressure. Still more specifically, the present invention relates to the improvement of stiffness or torquability of such devices. Those skilled in the art will recognize the benefits of applying the present invention to similar fields not discussed herein.

BACKGROUND OF THE INVENTION

Angioplasty procedures have gained wide acceptance in recent years as efficient and effective methods for treating many types of vascular disease. In particular, angioplasty is widely used for opening stenosis or occlusions in the coronary arteries, although it is also used for the treatment of stenosis in other parts of the vascular system.

The most widely used form of angioplasty makes use of a dilation catheter which has an inflatable balloon at its distal end. Inflation of the balloon at the site of the occlusion causes a widening of the vessel to reestablish an acceptable blood flow through the vessel.

It often is desirable to determine the severity of the occlusion in order to properly choose a dilation catheter or to make a determination as to whether treatment is required at all. Various techniques have been used to determine the severity of the occlusion. One way of determining the severity of the occlusion is to measure pressure at points both proximal to and distal of the occlusion.

Devices that are used for this purpose include catheter-like members with some type of pressure-sensing device incorporated therein. Such devices often referred to a pressure-sensing guidewire since they can provide the dual function of guidewire and a pressure measuring device. One known device measures the pressure as a function of the deflection of a diaphragm located at the proximal end of the catheter. Examples of intravascular pressure-sensing guidewires are illustrated in U.S. Pat. Nos. 5,873,835 and 5,836,835.

One problem associated with currently available pressure-sensing devices is the reduced function as a guidewire. Specifically, because the catheters or elongated tubes are hollow, they bend easily and are often difficult to maneuver, steer or control.

Accordingly, there is a need for an improved device which can function both as a pressure-sensing device and a guidewire with improved controllability. Still further, there is a need for an improved intravascular pressure-sensing device which can also serve as a guidewire but which has improved torque or stiffness without compromising the pressure-sensing capabilities of the device.

SUMMARY OF THE DISCLOSURE

The present invention overcomes the deficiencies of the prior art by providing a pressure-sensing guidewire assembly that comprises an elongated tubular member having a lumen extending through the member. The elongated tubular member further comprises an outer surface and an inner surface and at least one opening extending between the inner and outer surfaces and providing communication between the outer surface and the lumen. Pressure is communicated from the vascular environment outside of the lumen, through the opening and down the lumen to a transducer device connected to a proximal end of the elongated tubular member. In order to improve the performance of the pressure-sensing guidewire assembly to function as a guidewire, a torque enhancing mandrel is inserted into the lumen during the insertion of the assembly through a vessel or artery and the positioning of the assembly at the place of interest in the vascular system. To take a pressure measurement, the torque enhancing member is removed from the elongated tubular member and a pressure reading device such as a transducer is connected to a proximal end of the tubular member. Either the proximal or distal ends of the torque enhancing member and tubular member are detachably connected together.

In another embodiment, a method for increasing the stiffness or torquability of a pressure measuring device is provided which comprises providing an elongated tubular member having a lumen extending through the elongated tubular member. The elongated tubular member being a pressure-sensing guidewire. The method including the step of inserting a torque enhancing mandrel into the lumen and detachably connecting the torque enhancing member to the elongated tubular member to provide increased stiffness and torquability to the pressure-sensing guidewire.

DETAILED DESCRIPTION OF THE PRESENTLY PREFERRED EMBODIMENTS

Figure 1:
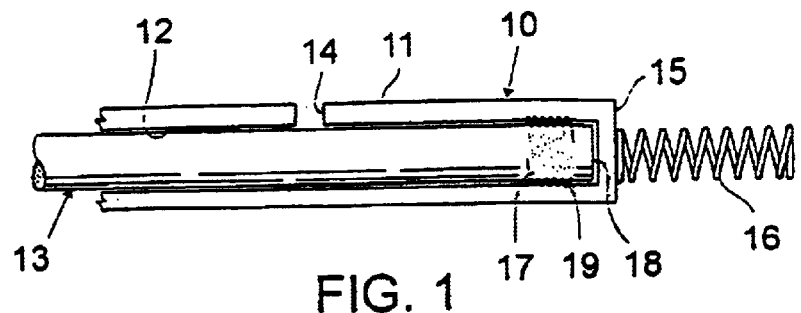
FIG. 1 is a side schematic view illustrating a distal end of a pressure-sensing guidewire equipped with a torque enhancing member.

Turning to FIG. 1, a distal end section of an elongated tubular member 10 is shown. The elongated tubular member includes an outer surface 11 and an inner surface 12 that defines a lumen. Received within the lumen is a torque enhancing mandrel 13. An opening 14 provides communication between the outer surface 11 or vascular environment and the lumen that is occupied by the torque enhancing member 13. The torque enhancing member 13 serves to improve the stiffness and torquability of the elongated tubular member 10 (or pressure-sensing guidewire) during insertion of the guidewire 10 into the vascular system and/or during the placement of the guidewire 10 at the place of interest in the vascular system.

In the embodiment shown in FIG. 1, the distal end 15 of the elongated tube 10 is closed and may optionally be connected to a spring tip 16 or other atraumatic tip. Also shown in FIG. 1 is the placement of threads 17 near the distal end 18 of the torque enhancing mandrel 13. The inside surface 12 of the elongated tubular member also includes threads 19 to threadably connect the distal end 18 of the torque enhancing mandrel 13 to the distal end 15 of the elongated tubular member 10. Such a detachable connection is useful in improving the stiffness or torquability of the elongated tubular member 10.

Figure 2:
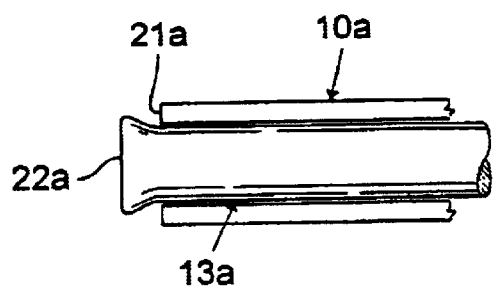
FIG. 2 is a side schematic view of proximal ends of a pressure-sensing guidewire and torque enhancing member.
Figure 3:
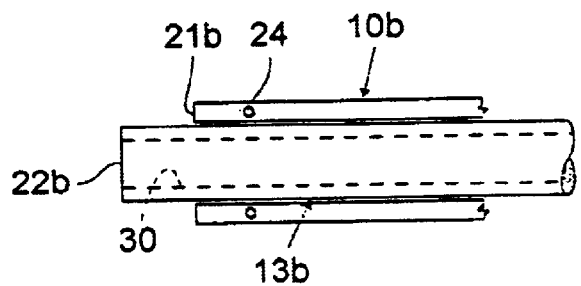
FIG. 3 is a side schematic view of the proximal ends of yet another pressure-sensing guidewire and torque enhancing member.

Turning to FIGS. 2–5, it has also been found that it is useful to connect the proximal ends of the elongated tubular member 10 and torque enhancing mandrel 13 together for improved stiffness and torquability. Referring to FIG. 2, the proximal end 21a of the elongated tubular member 10a receives a wedged proximal end 22a of the torque enhancing mandrel 13a to provide a tight friction fit. Referring to FIG. 3, the proximal end 21b of the elongated tubular member 10b is fused to the proximal end 22b of the torque enhancing member 22b. The proximal end 21b of the tubular member 10b also includes a coil 24. To disconnect the tubular member 10b from the torque enhancing member 22b, current is applied to the coil 24 which causes the coil 24 to melt the fused proximal end 21b of the elongated tubular member 10b thereby releasing the grip on the proximal end 22b of the torque enhancing mandrel 13b. FIG. 3 also illustrates a torque enhancing mandrel 13b with a lumen 30. It will be noted that the torque enhancing members may be solid or tubular.

Figure 4:
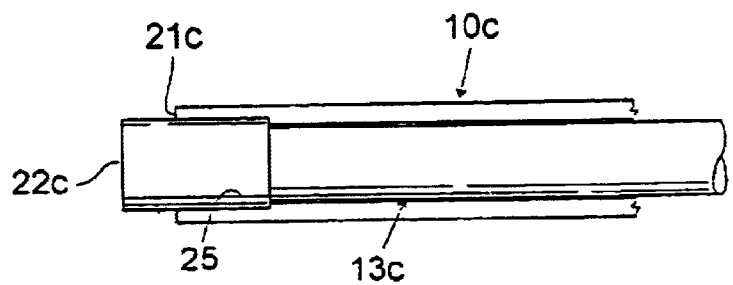
FIG. 4 is a side schematic view of yet another pressure-sensing guidewire equipped with a torque enhancing member.
Figure 5:
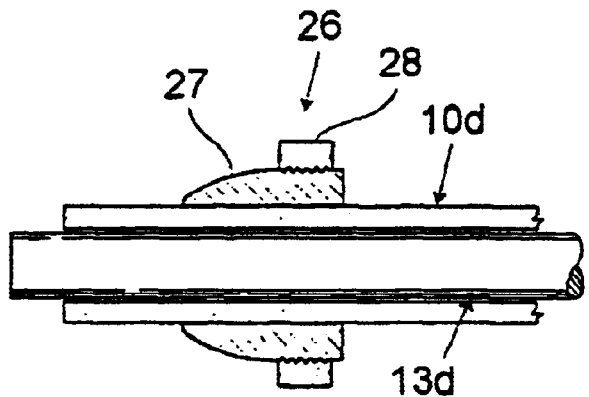
FIG. 5 is a side schematic view of yet another pressure-sensing guidewire equipped with a torque enhancing member.

Referring to FIG. 4, the proximal end 21c of the elongated tubular member 10c includes an enlarged step 25 for frictionally receiving the enlarged proximal end 22c of the torque enhancing member 13c. In FIG. 5, a clamping device 26 is utilized which includes a collet 27 through which the elongated tubular member 10d is fed. A retaining or compression nut 28 is screwed onto the collet 27 thereby causing the collet 27 to grip radially inwardly against the elongated tubular member 10d thereby causing the elongated tubular member 10d to clamp radially inwardly against the torque enhancing member 13d in a manner similar to a drill chuck.

Figure 6:
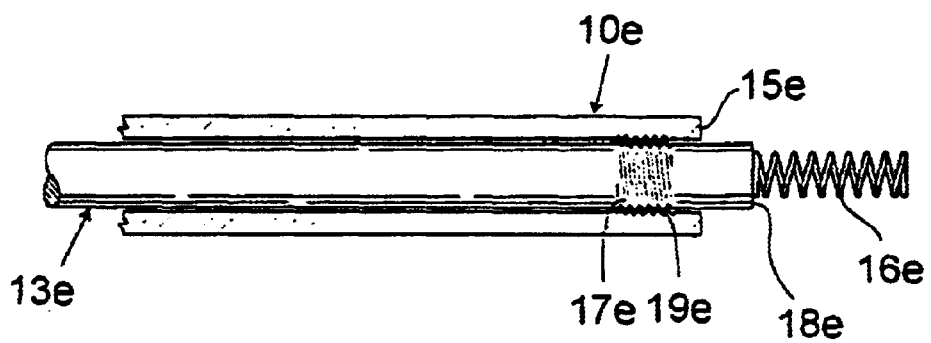
FIG. 6 is a side schematic view of distal ends of another pressure-sensing guidewire and torque enhancing member.

Turning to FIG. 6, it will be noted that the torque enhancing mandrel 13e may include a spring tip 16e at its distal end 18e. In this embodiment, the elongated tubular member 10e would not include holes in the side such as the one shown at 14 in FIG. 1. Instead, the pressure reading would be conducted through the open distal end 15e of the elongated tubular member 10e. To improve the torquability, a threaded connection between the distal ends 15e, 18e is provided by way of the threads 17e and 19e.

Figure 7:
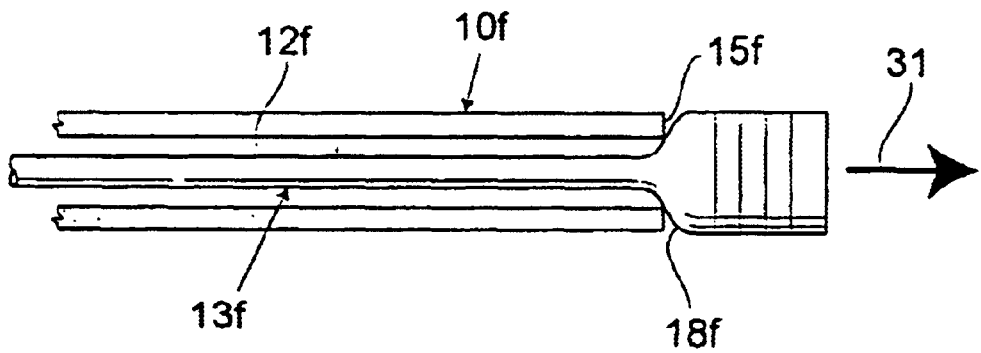
FIG. 7 is a side schematic view of distal ends of another pressure-sensing guidewire and torque enhancing member.

FIG. 7 illustrates the distal end 15f of an elongated tubular member 10f wherein the distal end 15f is engaged by an enlarged distal end 18f of a torque enhancing mandrel 13f. Instead of requiring the elongated tubular member 10f to include side openings such as 14 shown in FIG. 1, the torque enhancing mandrel 13f can be slide forward or distally in the direction of the arrow 31, thereby opening communication through the distal end 15f of the elongated tubular member 10f and into the lumen 12f. The pressure is communicated down the lumen 12f to the proximal end (not shown) and sensed by a pressure measuring device (not shown).

Figure 8:
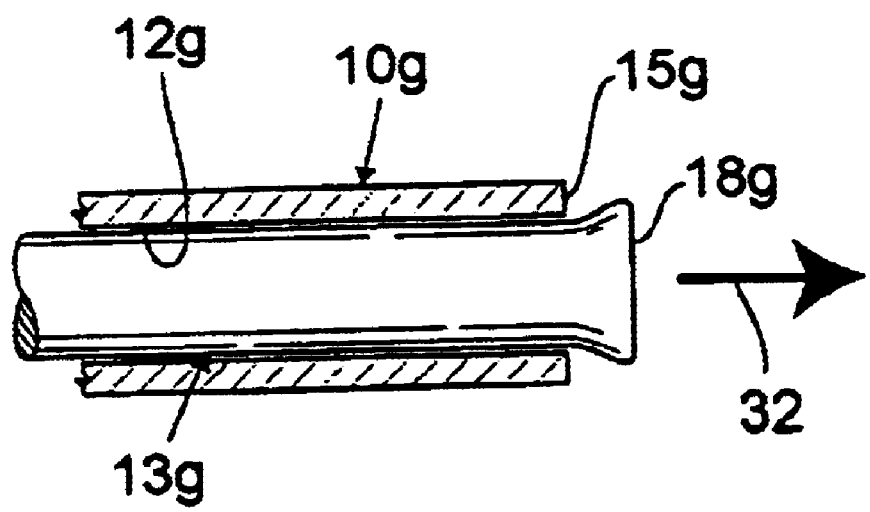
FIG. 8 is a side schematic view of distal ends of another pressure-sensing guidewire and torque enhancing member.

FIG. 8 illustrates the distal end 15g of an elongated tubular member 10g that receives a wedge distal end 18g of a torque enhancing mandrel 13g. Again, instead of requiring side openings such as 14 shown in FIG. 1, the torque enhancing mandrel 13g may be slid forward in the direction of the arrow 32 to provide communication through the distal end 15g of the elongated tubular member 10g and into the lumen 12g defined by the elongated tubular member 10g.

Figure 9:
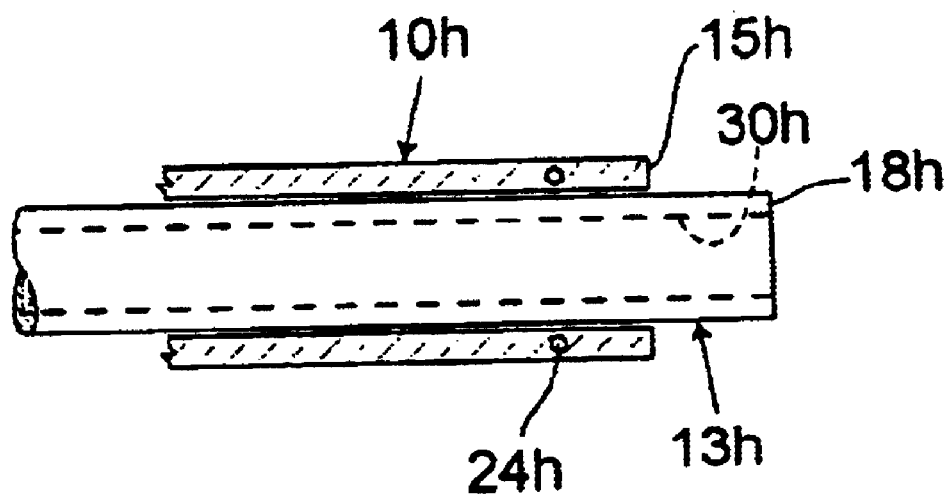
FIG. 9 is a side schematic view of distal ends of yet another pressure-sensing guidewire and torque enhancing member.

Similar to FIG. 3, FIG. 9 illustrates a torque enhancing mandrel 13h with a lumen 30h extending therethrough. The distal end 15h of the elongated tubular member 10h includes a coil 24h which is used to fuse the distal end 15h of the elongated tubular member to the distal end 18h of the torque enhancing mandrel 13g.

The materials from which the torque enhancing members can be made vary greatly. Suitable metals and metallic alloys will be apparent to those skilled in the art. For example, metallic alloys such as Inconel 617™, Inconel 625™, Hastelloy S™, Hastelloy X™, Nimonic 90™, Incoloy 800™, MP35-N Elgiloy™, 304LV™, 316 LVM™, Aermet 100™, Aermet 310™, CRB-7™, Custom 450™, Custom 455™, Custom 465m™, NiMark 250™, NiMark 250 NCO™, NiMark 300™, Nickel 200™, 304LV™, 316 LVM™, 321™, 347™, Aermet 100™, Aermet 310™, Haynes 214™, Haynes 230™, Inconel 600™, Inconel 601™, Inconel 617™, Inconel 625™, RA 333™, Hastelloy B™, Hastelloy N™, Hastelloy S™, Hastelloy W™, Hastelloy X™, Hastelloy C-276™, Haynes HR-120™, Haynes HR-160™, Nimonic 75™, Nimonic 86™, Haynes 556™, Incoloy 800™, Incoloy 800H™, Incoloy 800H™, Incoloy 801™, Incoloy 802™, MP35-N™ and Elgiloy™ can be utilized.

While the specification describes preferred designs and methods, those skilled in the art will appreciate the spirit and scope of the invention with reference to the appended claims.

What is claimed:

1. A guidewire assembly for use with a pressure-sensing device comprising:

an elongated tubular member having a lumen extending through the elongated tubular member, the elongated tubular member further comprising an outer surface, an inner surface and at least one opening extending between the inner and outer surfaces and providing communication between the outer surface and the lumen, the elongated tubular member further comprising a proximal end and a distal end, a torque enhancing mandrel received in the lumen, the torque enhancing mandrel further comprising a proximal end and a distal end, at least one of the proximal ends or the distal ends of the torque enhancing mandrel and elongated tubular member being detachably connected by a detachable connection mechanism selected from the group consisting of:

the proximal end of the torque enhancing mandrel comprising an enlarged wedge that is frictionally received in the proximal end of the elongated tubular member;

the proximal ends of the elongated tubular member and torque enhancing member being detachably fused;

the proximal ends of the elongated tubular member and torque enhancing member being clamped together;

the proximal ends of the elongated tubular member and torque enhancing member are threadably connected;

the distal ends of the elongated tubular member and torque enhancing member being threadably connected;

the distal end of the torque enhancing mandrel comprising an enlarged wedge that is frictionally received in the distal end of the elongated tubular member; and the distal ends of the elongated tubular member and torque enhancing member being detachably fused.

2. The guidewire assembly of claim 1 wherein the proximal ends of the torque enhancing member and tubular member are detachably connected.

3. The guidewire assembly of claim 1 wherein the distal ends of the elongated tubular member and torque enhancing member being detachably connected.

4. The guidewire assembly of claim 1 wherein the torque enhancing mandrel is solid.

5. The guidewire assembly of claim 1 wherein the torque enhancing mandrel is made from stainless steel.

6. The guidewire assembly of claim 1 wherein the torque enhancing member is made from solid stainless steel.

7. The guidewire assembly of claim 1 wherein the torque enhancing member is tubular.

8. The guidewire assembly of claim 1 wherein the elongated tubular member is made from an alloy comprising nickel and titanium.

9. A guidewire assembly for use with a pressure-sensing device comprising:

an elongated tubular member having a lumen extending through the elongated tubular member, the elongated tubular member further comprising an outer surface, an inner surface and at least one opening extending between the inner and outer surfaces and providing communication between the outer surface and the lumen, the elongated tubular member being fabricated from Nitinol, a torque enhancing mandrel received in the lumen, the torque enhancing mandrel being fabricated from stainless steel, the elongated tubular member further comprising a proximal end and a distal end, the torque enhancing mandrel further comprising a proximal end and a distal end, and the proximal ends of the elongated tubular member and torque enhancing member being detachably connected by a detachable connection mechanism selected from the group consisting of:

the proximal end of the torque enhancing mandrel comprising an enlarged wedge that is frictionally received in the proximal end of the elongated tubular member;

the proximal ends of the elongated tubular member and torque enhancing member being detachably fused;

the proximal ends of the elongated tubular member and torque enhancing member being clamped together; and the proximal ends of the elongated tubular member and torque enhancing member are threadably connected.

10. The guidewire assembly of claim 9 wherein the distal ends of the elongated tubular member and torque enhancing member being detachably connected by a detachable connection mechanism selected from the group consisting of:

the proximal ends of the elongated tubular member and torque enhancing member are threadably connected;

the distal ends of the elongated tubular member and torque enhancing member being threadably connected;

the distal end of the torque enhancing mandrel comprising an enlarged wedge that is frictionally received in the distal end of the elongated tubular member; and the distal ends of the elongated tubular member and torque enhancing member being detachably fused.

11. The guidewire assembly of claim 9 wherein the torque enhancing mandrel is solid.

12. The guidewire assembly of claim 9 wherein the torque enhancing mandrel comprises a distal end connected to a spring tip.

13. A method for increasing the stiffness of a pressure measuring device that comprises an elongated tubular member having a lumen extending through the elongated tubular member, the elongated tubular member further comprising an outer surface, an inner surface and at least one opening extending between the inner and outer surfaces and providing communication between the outer surface and the lumen, the elongated tubular member further comprising a proximal end and a distal end, the method comprising:

inserting a torque enhancing mandrel comprising a proximal end and a distal end into the lumen, detachably connecting at least one of the proximal ends or the distal ends of the torque enhancing member and elongated tubular member together with a detachable connection mechanism selected from the group consisting of:

the proximal end of the torque enhancing mandrel comprising an enlarged wedge that is frictionally received in the proximal end of the elongated tubular member;

the proximal ends of the elongated tubular member and torque enhancing member being detachably fused;

the proximal ends of the elongated tubular member and torque enhancing member being clamped together;

the proximal ends of the elongated tubular member and torque enhancing member are threadably connected;

the distal ends of the elongated tubular member and torque enhancing member being threadably connected;

the distal end of the torque enhancing mandrel comprising an enlarged wedge that is frictionally received in the distal end of the elongated tubular member; and the distal ends of the elongated tubular member and torque enhancing member being detachably fused.

14. A guidewire assembly for use with a pressure-sensing device comprising:

an elongated tubular member having a lumen extending therethrough, the elongated tubular member comprising an open distal end and a proximal end, a torque enhancing mandrel received in the lumen and comprising a distal end that extends beyond the distal end of the elongated tubular member, the distal end of the torque enhancing mandrel comprising a spring tip, the torque enhancing member further comprising a proximal end, at least one of the proximal and distal ends of the torque enhancing member and elongated tubular member being detachably connected.

15. A method of measuring pressure within a patient's vasculature system, the method comprising:

providing a pressure measuring device that comprises an elongated tubular member having a lumen extending through the elongated tubular member, the elongated tubular member further comprising an outer surface, an inner surface and at least one opening extending between the inner and outer surfaces and providing communication between the outer surface and the lumen, the elongated tubular member further comprising a proximal end and a distal end;

inserting an elongated torque enhancing member comprising a proximal end and a distal end into the lumen of the elongated tubular member;

detachably connecting at least one of the proximal ends or the distal ends of the torque enhancing member and elongated tubular member together with a detachable connection mechanism selected from the group consisting of:
  the proximal end of the torque enhancing mandrel comprising an enlarged wedge that is frictionally received in the proximal end of the elongated tubular member;
  the proximal ends of the elongated tubular member and torque enhancing member being detachably fused;
  the proximal ends of the elongated tubular member and torque enhancing member being clamped together;
  the proximal ends of the elongated tubular member and torque enhancing member are threadably connected;
  the distal ends of the elongated tubular member and torque enhancing member being threadably connected;
  the distal end of the torque enhancing mandrel comprising an enlarged wedge that is frictionally received in the distal end of the elongated tubular member;
  the distal ends of the elongated tubular member and torque enhancing member being detachably fused;
inserting the distal end of the elongated tubular member into the patient's vasculature system leaving the proximal end of the elongated tubular member and proximal end of the torque enhancing member outside of the patient's vasculature system;
disengaging the torque enhancing member from the elongated tubular member; and
connecting a pressure measuring device to the proximal end of the elongated tubular member and measuring fluid pressure communicated through the lumen thereof.

* * * * *

UNITED STATES PATENT AND TRADEMARK OFFICE
CERTIFICATE OF CORRECTION

PATENT NO. : 6,652,471 B2
DATED : November 25, 2003
INVENTOR(S) : Timothy G.J. Ehr et al.

It is certified that error appears in the above-identified patent and that said Letters Patent is hereby corrected as shown below:

<u>Title page,</u>
Item [73], Assignee, please delete "SciMed" and replace with -- Scimed --.

Signed and Sealed this

Thirtieth Day of March, 2004

JON W. DUDAS
*Acting Director of the United States Patent and Trademark Office*